United States Patent
Kolari et al.

(10) Patent No.: US 11,859,347 B2
(45) Date of Patent: Jan. 2, 2024

(54) METHOD FOR PREDICTING OR CONTROLLING MICROBIAL STATUS OF A PAPER OR BOARD MAKING PROCESS

(71) Applicant: Kemira Oyj, Helsinki (FI)

(72) Inventors: Marko Kolari, Vantaa (FI); Marjatta Piironen, Espoo (FI); Iiris Joensuu, Espoo (FI)

(73) Assignee: Kemira Oyj, Helsinki (FI)

(*) Notice: Subject to any disclaimer, the term of this patent is extended or adjusted under 35 U.S.C. 154(b) by 538 days.

(21) Appl. No.: 16/770,627

(22) PCT Filed: Dec. 7, 2018

(86) PCT No.: PCT/FI2018/050887
§ 371 (c)(1),
(2) Date: Jun. 8, 2020

(87) PCT Pub. No.: WO2019/110876
PCT Pub. Date: Jun. 13, 2019

(65) Prior Publication Data
US 2020/0299903 A1 Sep. 24, 2020

(30) Foreign Application Priority Data
Dec. 8, 2017 (FI) .................................... 20176099

(51) Int. Cl.
*D21H 21/36* (2006.01)
*D21B 1/34* (2006.01)
(Continued)

(52) U.S. Cl.
CPC .............. *D21H 21/36* (2013.01); *D21B 1/32* (2013.01); *D21B 1/345* (2013.01); *D21C 9/008* (2013.01);
(Continued)

(58) Field of Classification Search
CPC ........ D21H 21/36; D21H 21/02; D21B 1/345; D21D 5/28; D21G 9/0018
See application file for complete search history.

(56) References Cited

U.S. PATENT DOCUMENTS

| 8,444,858 B2 | 5/2013 | Barak |
| 2014/0000486 A1 | 1/2014 | Buri |

FOREIGN PATENT DOCUMENTS

| EP | 1010804 A1 | 6/2000 |
| EP | 2115157 B1 | 11/2009 |

(Continued)

OTHER PUBLICATIONS

Jokinen, K.: "Paper machine microbiology". In: Papermaking Chemistry, Papermaking Science and Technology, Book 4, Ediited by Neimo, L. Jyväskylä: Fapet Oy, 1999, ISBN 952-5216-04-7, pp. 261-264.

(Continued)

*Primary Examiner* — Anthony Calandra
(74) *Attorney, Agent, or Firm* — Meunier Carlin & Curfman LLC (57) ABSTRACT

A method is disclosed for predicting the microbial status of a paper or board making process and/or quality of the dry board or paper obtained from the process for controlling microbial status of a paper or board making process or quality of the dry board or paper obtained from the process. Surface level and duration of time in at least one storage tower or pulper are monitored and correlated with respective predetermined values for the tower or pulper in order to predict the risk of microbial activity.

5 Claims, 6 Drawing Sheets

(51) Int. Cl.
    *D21C 9/00*      (2006.01)
    *D21D 5/28*      (2006.01)
    *D21G 9/00*      (2006.01)
    *D21H 21/02*     (2006.01)
    *G01N 33/34*     (2006.01)
    *D21B 1/32*      (2006.01)
(52) U.S. Cl.
    CPC .............. *D21D 5/28* (2013.01); *D21G 9/0018* (2013.01); *D21H 21/02* (2013.01); *G01N 33/343* (2013.01)

(56) References Cited

FOREIGN PATENT DOCUMENTS

| | | |
|---|---|---|
| EP | 2748373 | 2/2013 |
| EP | 2851466 A1 | 3/2015 |
| JP | 2016172949 A | 9/2016 |
| WO | 00/50695 A1 | 8/2000 |
| WO | 03025279 A1 | 3/2003 |
| WO | 2007125154 A1 | 11/2007 |
| WO | 2008028771 A1 | 3/2008 |
| WO | 2013079801 A1 | 6/2013 |
| WO | 2014001051 A1 | 1/2014 |
| WO | WO-2015156512 A1 * 10/2015 ......... B01D 21/0012 |

OTHER PUBLICATIONS

Search Report of corresponding Russian application RU2020118932, dated Jan. 15, 2022, 4 pages.
Office Action from Intellectual Property India in corresponding application 202017023981 in India, dated May 24, 2022, 7 pages.

* cited by examiner

METHOD FOR PREDICTING OR CONTROLLING MICROBIAL STATUS OF A PAPER OR BOARD MAKING PROCESS

PRIORITY

This application is a U.S. national application of the international application number PCT/FI2018/050887 filed on Dec. 7, 2018 and claiming priority of Finnish national application number 20176099 filed on Dec. 8, 2017 the contents of all of which are incorporated herein by reference.

FIELD OF THE DISCLOSURE

This disclosure relates to a method for predicting the microbial status of a paper or board making process or for predicting quality of the dry board or paper obtained from said process and methods for controlling microbial status of a paper or board making process or quality of the dry board or paper obtained from said process.

BACKGROUND

Water-intensive processes such as papermaking offer a fertile environment for microbiological growth. Without proper control microbial contaminants can grow on paper machine surfaces as slimy deposits (biofilms) that will cause paper quality defects (dirt spots, holes) or break the paper web forcing the machine to be stopped for cleaning. Defects can cause costly quality complaints from end-users of the paper. Extra cleaning stops will cause production losses and lower the cost-efficacy of paper manufacturing. Large volume storage towers for water and pulp can support intensive growth of microorganisms, causing formation of e.g. acids that lower process pH, compounds with bad odors or thermotolerant bacterial spores. The amount of spores in the final paper or board product should be as low as possible, if the product is intended for purposes such as food or beverage packaging.

Due to all these problems that microorganisms can cause, biocidal treatments are often necessary in the water-intensive papermaking processes. Water volumes in modern paper or board machine can exceed tens of thousands cubic meters. Therefore, the aim with biocides usually is not a complete system-wide sterilization of the whole process, but a contribution for finding a stable process situation with control of microbial growth on an acceptable and cost-efficient level.

Microbe control applications in paper and board machines have utilized on-line monitoring for parameters such as pH or dissolved oxygen for years. However, it is not possible to take representative samples from the contents in large broke/storage towers with a volume of thousands of cubic meters, as the pulp within the towers does not get evenly mixed. And still a microbial contamination in just one storage tower or one pulper may result in problems in downstream process and collapse quality of final product within 20 minutes to couple of hours after the contaminated pulp leaves the storage. It is thus evident that there is a need for improved methods for microbe control in storage towers and pulpers which diminish the risk of low quality paper production or unplanned machine stops for restoring the microbial status of the process.

SUMMARY

The present disclosure generally relates to methods for predicting the microbial status of a paper and board making process and methods for preventive controlling said processes. The inventors have surprisingly been able to find that a combination of a surface level and time in a storage tower or broke tower or a pulper can be used for predicting a risk of microbial activity, in particular increasing risk of microbial activity in said tower and thereby for whole downstream process, and risk of producing lower quality final paper or board.

The first object of the invention is a method for predicting the microbial status of a paper or board making process or quality of the dry board or paper obtained from said process. According to the invention said method comprises monitoring surface level and duration of time in at least one pulp storage tower, broke storage tower or broke pulper, wherein a detection that the surface level has not met (i.e. has been above of) the predefined limit for the surface level during a predefined duration of time is indicative of risk of higher microbial activity in said process.

The second and the third object of the invention are methods for controlling microbial status of a paper or board making process or quality of the dry board or paper obtained from said process.

DETAILED DESCRIPTION

In a process of making paper (including tissue) or board pulp enters a storage tower (or broke enters to broke tower) via the top of said tower and partially mixes with existing pulp as a consequence of the free fall into existing pulp volume. The pulp is taken to further process steps from the lower part of the tower. Mixing in large pulp towers is never perfect. In such towers, there are typically fast flowing zones (e.g. areas of entry of new pulp), slow flowing zones and probably also zones or areas where the movement of pulp is minimal or zero. Pulp in slowly flowing zones is particularly susceptible to microbial growth and may serve as source for larger scale microbial contamination within said tower and then in every down-stream process step after said tower.

Pulp storages in pulp mills and pulp or broke storages in paper and board machines, usually towers or tanks into which pulp is fed, are fed from the upper part of the tower/tank and emptied from near the bottom. The tower usually has mixing blades at the bottom of the tower. It is rather common that in large pulp or broke towers only the lowest 15-20% volume can be effectively mixed by these blades. The towers come in different dimensions, but are typically upwards standing cylinder like vessels with a ratio of the inner diameter to the inner height less than 1:1.5.

In this connection term "tower" should be understood to cover both pulp storage towers and broke storage towers, unless otherwise indicated.

Here term "pulp" refers to pulp suspension comprising at least cellulosic fibers and water, and possibly conventional paper making additives. Pulp may be mechanical pulp, chemical pulp or recycled pulp or any combination thereof. In addition to those broke (broke pulp) comprises paper or board (coated or uncoated) that was discarded at any stage during its manufacture and is re-pulped in a broke pulper for reuse in making of new paper or board.

In manufacturing and bleaching of pulp the consistency maybe higher than 10 wt % (fibers per water), whereas in the paper or board making process the typical consistency of pulp suspension in pulp or broke storage towers is below 10 wt-%. Pulpers and towers where broke is collected may have consistency of 1 to 3 wt-%. In order to reduce the volume for storage towers the consistency of pulp or broke may be increased by thickening to 4 to 10 wt-%, typically about 6 to 8 wt-%. Consistency may be increased by removing the water using conventional methods with the art.

The inventors have found a correlation between the delay in emptying a storage tower or a pulper or lowering a surface level of a storage tower or a pulper (in other words prolonged duration of time when the surface level of pulp in said tower exceeds a predefined limit for the surface level) and an increase in risk of problems caused by microbial contaminants, such as bacteria or spores, in down-stream processes. The inventors have shown that the microbiological quality of pulp starts to get worse at surface levels above 30 to 40% (of the height of the tower), especially when the level is constantly above said level. There may be cases where the microbiological quality of pulp starts to get worse at sometimes even above 25% of the height of the tower, or even at lower surface levels. When the surface level in a tower is above the volume impacted by the bottom mixer blades the incoming pulp entering said tower from top will not be sufficiently mixed with all existing pulp. Slow flowing zones will be formed, and this may increase the bacterial growth and spore formation in said tower or pulper.

It has now been found that lowering the tower surface level to a predetermined level (or below it) at the latest when reaching the predetermined duration of time is an effective way to control the microbial conditions in the downstream flow and following process steps in the pulp or papermaking process or to control the quality of the produced paper. The present methods allow preventive microbial control and hygiene maintenance and thus reduce losses caused by low quality final paper or board. The method can also reduce need of extensive use of controlling chemicals (environmental and economic aspect) and even maintenance breaks (environmental and economic aspect). A further advantage is that microbial status of the process and quality of the end product (pulp or paper) can be proactively effected instead of acting solely when the microbes are already causing some problems in the process or in the end-product quality, or the microbe control in the process is completely out of control. Unless being able to predict and/or affect microbial conditions proactively in a process, a pulp severely spoiled by bacteria in one location will affect the microbial activity in all downstream process steps, if not isolated from other streams or locations.

In this connection expressions "surface level" and "tower level" refer to the surface level of pulp or other fibrous aqueous mass in a tower or a pulper. The level is given as a percentage of the inner height of said tower or pulper. The inventors have shown that a so called "risk limit" for said surface level can be determined as a predefined limit for the surface level for at least most of the towers or pulpers involved in the process. The risk limit for surface level is dependent on e.g. the mixer efficacy, structural design and pulp consistency in said tower or pulper.

In this connection expression "duration of time" refers to residence time of a pulp suspension (such as pulp or broke) in a tower or pulper. According to this invention the duration of time is measured in relation to the surface level of the pulp suspension in said tower or pulper. Calculation of duration of time starts when the surface level exceeds (is above of) the predefined limit for surface level (risk limit for surface level). Recording the duration of time continues until the tower surface level again meets the predefined limit for the surface level. When the surface level of the pulp suspension in a tower or tank is below the predefined level, duration of time is zero.

Typically, duration of time is measured using a timer receiving online information of the surface level in said tower. The timer starts to record the time when the surface level exceeds the predefined limit for the surface level. The timer is on and calculating the time until the level meets the predefined surface level. When the surface level in a tower or tank is below the predefined level, the timer is off and not calculating the time. The recorded time remains as zero until the surface level exceeds the predefined limit for the surface level again.

Predefined duration of time for a tower or pulper in this connection is a time that is deemed not indicating a risk of higher microbial activity in said tower or said pulper over a level that could worsen the microbial status of the paper making process or reduce quality of the dry paper or board obtained from said process. In case a predefined duration of time is exceeded, risk for higher microbial activity may be increased. The predefined limit for duration of time of is dependent on e.g. quality of pulp (especially microbiological activity level) in said tower or said pulper, overall process status and also the requirements of the paper or board obtainable from said process. For example, a predefined limit for duration of time for storage tower for new pulp is often longer than respective time limit for broke in a broke tower, as microbe content of broke is often higher than in fresh pulp.

The predefined limit for the surface level is dependent on e.g. quality of pulp (especially microbiological activity level) in said tower or said pulper, overall process status and also the requirements of the paper or board obtainable from said process. The risk limit for surface level is typically dependent on e.g. the mixer efficacy, structural design and pulp consistency in said tower or pulper.

If tower surface level has not been lowered to or below a risk limit, also discussed as "predefined limit for the surface level" (in other words, if the tower surface level has been above the predefined limit for the surface level) during a predefined time (predefined duration of time), it is believed that the risk that the pulp gets contaminated is increased. If tower surface level has not been lowered to or below a predefined limit during a predefined duration of time, the slowly moving pulp may potentially be contaminated and said contaminated pulp may exit the tower or pulper when the tower or pulper is lowered to or below said predefined limit for surface level next time.

According to the present invention a method for predicting microbial status of a paper or board making process or quality of the dry board or paper obtained from said process comprises monitoring surface level and duration of time in at least one pulp storage tower, broke storage tower or broke pulper. A detection that the surface level which is above the predefined limit for the surface level has not met a predefined limit for the surface level, that can also be called 'a risk limit', during a predefined time (predefined duration of time) is indicative of risk (or increase in risk) of higher microbial activity in said process. In other words, a detection that the tower has not been emptied or lowered to or below a predefined limit for the surface level during a predefined time is indicative of risk, or increase of risk of higher microbial activity in said process.

Higher microbial activity in one location may increase the microbial activity in all downstream process steps. Spore formation during paper or board making process compromises the quality of a resulting paper or board especially in high hygiene food-packaging end uses. In addition, high microbial activity in process can lower the quality of the finished dry paper or board and can cause economic challenges. Such quality issues can be caused by high microbial activity that lowers process pH to a level that disturbs paper making chemistry. High microbial activity can produce compounds with bad odor which will stick to final dry paper or board. Biofilm formed by viable bacterial or fungal cells on machine surfaces can result in runnability problems and dirt spots in finished paper or board.

Microbiological status of process used herein refers to number of viable bacterial cells, viable fungal cells, and number of bacterial endospores present in pulp, broke or in circulating water. Microbial status of process used herein refers also to amount of biofilm formed by microbes on machine surfaces. Microbial status of process used herein refers also to amount of possible malodorous microbial metabolites, such as volatile fatty acids (VFA) in the process. Microbial status of process used herein refers also to possible physicochemical changes caused by microbes in process, such as change in pH or ORP (Redox) of the process.

Higher microbial activity in this connection means one or more of the following: higher number of microorganisms (higher meaning a change of at least 1 log unit), higher amount of biofilm, formation of malodorous compounds, lower pH (e.g. change of at least 0.2 pH units), lower redox (e.g. change of at least 40 mV) when compared to an acceptable level for an individual paper or board making process. An acceptable level for an individual paper or board making process varies according to for example quality and type of incoming raw material and requirements of dry paper or board obtained from said process.

The present disclosure can also be described as a method for predicting the microbial status of a paper or board making process or quality of the dry board or paper obtained from said process comprising monitoring surface level and duration of time in at least one pulp storage tower, broke storage tower or broke pulper. A detection that the surface level of the tower has not been lowered to or below predefined limit for the surface level during a predefined time is indicative of increase in risk of higher microbial activity in said process.

In one embodiment the surface level is monitored in at least two of storage towers, broke towers or pulpers. A detection that the surface level is monitored in at least two storage towers, broke towers or pulpers, wherein a detection that the surface levels of at least two storage towers, broke towers or pulpers has not met (in other words has been above) the predefined limit for the surface level, i.e. so-called risk limit for surface level, during the predefined time is indicative of an increase in the risk of higher microbial activity in said tower or pulper. A wider spread or severe increase in microbial activity is more likely to result in the downstream process and risk for quality problems increases.

In one embodiment predefined limit for the surface level of a tower or a pulper and predefined time are defined based on historical data obtained from said tower or pulper in relation to historical data obtained from one or more key performance indicators (KPIs) of said process or from dry paper or board obtained from said process, wherein the historical data obtained from said tower or pulper comprises at least one data set representing the surface level of said tower or said pulper as a function of time in relation to historical data of at least one key performance indicator (KPI) of said process or of dry paper or board obtained from said process.

Time period for data set collection varies in different paper or board making systems. Preferably historical data from a paper or board making process is collected during at least one week. The longer the data collection time, the more precise or accurate correlation is available.

In one embodiment the predefined limit for the surface level for a pulp storage tower is 35%, preferably 30% and more preferably 25% or 20%. In one embodiment the predefined limit for the surface level for a broke tower is 40% or 35%, preferably 30%, more preferably 25% or 20%, and still more preferably 15% or even 10%. In one embodiment the predefined limit for the surface level for a pulper is 30%, preferably 20%.

In one embodiment the predefined limit for said time in storage tower is 3 days, preferably 2 days. In one embodiment the predefined limit for time in a broke tower is 2 days, preferably 1 day. In one embodiment, the predefined limit for said time in a pulper is 24 hours, preferably 20 hours. In another embodiment said time is 18 hours, preferably 12 hours.

In one embodiment the predefined limit for the surface level for a pulp storage tower is 30%, preferably 20% and respectively the predefined limit is 72 hours, preferably 36 hours.

In one embodiment the predefined limit for the surface level for a broke tower is 25%, preferably 15% and respectively the predefined limit is 40 hours, preferably 20 hours.

In one embodiment the predefined limit for the surface level for a broke tower is 40%, preferably 35% and respectively the predefined limit is 168 hours, preferably 120 hours.

In one embodiment the predefined limit for the surface level for a pulper is 30%, preferably 20% and respectively the predefined limit is 48 hours, preferably 24 hours.

Different measurements indicating or measuring surface level in various vessels are used in industry, including paper or board making processes. A person skilled in the art understands that surface level measurements may be calibrated in another ways, depending on e.g. the material to be measured and/or shape of the vessel, such as tower, tank or pulper. Surface level of a vessel may be given for example, as percentages of the height of a vessel (such as tower or pulper) or as a percentage of maximum filling level of said vessel. Thus, a surface level measurement may be calibrated e.g. in a way that 100% surface level equals with the vessel height or that 100% surface level equals with maximum filling level of the vessel.

Surface levels above are given as percentages of the height of the tower. However, those percentage values are also applicable for situations when surface levels are calibrated in a different way, e.g. provided as percentages indicating a percentage of the maximum filling level of a vessel (tower or tank or pulper), or in other way used in the field of the present disclosure.

The measurement technique of measuring the surface level is not essential for the invention. It is not essential which way surface level measurements have been calibrated for a vessel, as the surface level measurement techniques and ways of indicating surface level percentages in a vessel are well known in the industry and to a person skilled in the art. A predefined limit for the surface level ("risk limit") and/or a predefined duration of time indicating a risk or an increase in risk of higher microbial activity in said tower can be determined by monitoring said parameters (namely the surface level in relation to the of time) in said tower or pulper in relation to e.g. quality of resulting paper or board during several days, clustering the information obtained and concluding the correlation of values to each other. The historical data may be complemented by data derived from respective processes from other production sites but the final determination of risk limits for surface level and time is preferably based on data related to the particular tower or pulper.

In one embodiment, the calculation of risk level is based on a combination of a value from a timer (i.e. duration of time when the surface level has not met the predefined surface level or in other words a surface level has been above said predefined surface level) and surface level. Timer value depends on the online information from a tower surface level. Timer starts to record the time when the surface level has exceeded the predefined risk limit (safety limit). Recording the duration of time continues until the tower surface level meets the predefined risk limit. Timer resets the time to 0 seconds when the tower surface level meets a value of the predefined limit for the surface level. The surface level is deemed to meet the predefined limit of surface level when the surface level is on the same level or below than said predefined level. When the surface level of the pulp suspension in a tower or tank is below the predefined surface level, duration of time remains as zero. Timer starts to record the time again when the surface level exceeds the risk limit (predefined risk limit). For practical cases, it may sometimes be useful to set different risk levels based on a combination of a value from a timer and surface level. When the recorded time is below (less than) a predefined time, the risk level is defined being at a risk level 0. When the recorded time is close to the predefined time, the system (e.g. PC, PLC) gives warning (risk level may e.g. be called risk level 1). When the recorded time has met predefined time, the system gives alert (risk level 2).

Risk level calculations may be carried out e.g. in a programmable logic (PLC) or industrial PC or in other suitable system. Signal from a tower level sensor may be connected to programmable logic (PLC) or industrial PC. Risk level may be calculated continuously in the system (PLC or industrial PC).

In one embodiment, when the recorded time is less than 48 hours or 2 days, risk level is 0. When the risk level is 0, it is considered that there is no increased risk for microbial activity (compared to acceptable level) and no preventive actions are needed. If the recorded time is more than 2 days but less than 2.2 days, risk level is 1, whereby the system gives a warning. If the recorded time is equal to or more than 2.2 days, risk level is 2, whereby the system give an alert of increased risk for microbial activity and preventive actions are needed.

In one embodiment said KPI of said process is selected from pH, ORP (redox), pH corrected redox (rH), oxygen, dissolved oxygen, oxygen consumption, microbial amounts, microbial activity, amount of biofilm, or amount of malodorous compounds in process. In one embodiment KPI is defined as delta, i.e. change in between tower inlet and outlet, for example KPI is defined as delta rH in broke tower should be less than 1 unit.

The redox value is dependent on pH and temperature. Determination of rH value thus involves measurement of temperature, pH and redox value. The rH value may be determined (calculated) using the pH and redox potential using equation (1):

$$rH = 2*pH + 2*Eh*F/(c*R*T) \tag{1}$$

wherein F=Faraday constant ($9.64853399 \times 10^4$ C mol$^{-1}$, c=ln 10, T=temperature (K), Eh=redox potential measured with standard hydrogen electrode, and R=universal gas constant (8.314472 J K$^{-1}$ mol$^{-1}$). In one embodiment rH is determined using equation (1).

In one embodiment said KPI of paper or board obtained from said process is microbe content of said dry paper or board. In one embodiment said KPI of paper or board obtained from said process is the number of quality defects of said dry paper or board. In one embodiment said KPI of paper or board obtained from said process is the bacterial spore count of said paper or board obtained from said process. The number of paper/board quality defects may be measured as amount or size of dirt spots or holes in the paper of board obtained from said process.

In one embodiment the number of paper/board quality defects is measured as a bacterial spore count in the dry paper or board obtained from said process. For high hygiene applications such as food packaging the bacterial spore count is commonly regulated by national legislation or by requirements from converters of board to final packages. Common limits for living aerobic bacteria are for example maximum 1000 CFU, or maximum 250 CFU, per gram of dry board.

Delta rH (pH corrected change in redox value) is measured as a difference between aqueous fiber suspension's rH values before and after a storage tower for pulp, broke tower or a broke pulper. In a well-functioning process the value is close to zero. The smaller the difference between rH values before and after a storage tower, the better is the microbiological status in the storage tower and the smaller the risk is for higher microbial activity and subsequent process problems.

Measuring the concentration of dissolved oxygen is suitable, either as such or in combination with e.g. oxygen consumption data, for determining the amount of aerobic microbes in a sample. The higher the microbe level is, the higher the amount of oxygen consumed by the microbes is, provided that these microbes have a supply of nutrition. The more the aerobic microbes consume oxygen, the lower the concentration of dissolved oxygen in a sample representing the situation in a process. A dissolved oxygen measurement therefore directly describes whether the process is aerobic (oxygen present) or anaerobic (no oxygen present). In the context of the present invention this data can support the primary observation relating to surface level.

Typically, the microbial content of pulp derived from pulping processes has a low amount of living microbes whereas microbial count in broke pulp may be higher without sufficient biocide treatment. Thus, it is to be understood that the determination of risk limits for the surface level and/or a duration of predefined time and other parameters must also be done separately.

In one embodiment monitoring of surface level and duration of time of at least one tower or pulper or at least one KPI of said process or of paper or board obtained from said process is based on continuous monitoring, optionally with set alert value. Continuous monitoring allows setting alerts and thereby increases the accuracy of prediction.

In one embodiment, measuring one or more further KPI(s) is based on a single measurement (triggered by indication of risk or an increase in risk based on surface level in said tower).

One advantage of the above described method for predicting the microbial status of a paper or board making process is that it allows preventive microbial control with reasonable simple measures, without e.g. extensive use of biocides or compromised quality of the paper or board obtained. Reliable predictions allow proactive adaptation of process parameters and is beneficial in view of environmental and economic aspects.

According to one embodiment of the invention a method for controlling microbial status of a paper or board making process or quality of the dry board or paper obtained from said process. The method comprises the steps of:
 a) monitoring surface level and duration of time in at least one storage tower, broke tower or pulper in relation of at least one KPI of said process or paper or board obtained from said process; and
 b) collecting historical data of said process by determining a correlation between said surface level, duration of time and KPI; and
 c) defining limits for said surface level and said duration of time which indicate a risk or an increase in risk of higher microbial activity in said process; and
 d) monitoring surface level and duration of time of at least one storage tower, broke tower or pulper, wherein a detection that the surface level which is first above a predefined limit (so-called risk limit) has not met the predefined (risk) limit during a predefined time is indicative of risk or an increase in risk of higher microbial activity in said process; and
 e) if indication generated in step c shows increased risk, adjusting at least one property of the process of the paper making plant.

According to one embodiment of the invention a method for controlling microbial status of a paper or board making process or quality of the dry board or paper obtained from said process comprises the steps of
 a) predicting microbial status of a paper or board making process or quality of the dry board or paper obtained from said process here described; and
 b) if risk or an increase of risk is predicted, adjusting at least one property of the process of the paper making plant.

The property to be adjusted can be e.g. a chemical treatment such as biocide feed or a change in pulp flow in said process.

In one embodiment one or more of the following adjustments to the process are made a) biocide feed quantity is increased into the tower and/or any process step before or after said tower or pulper where increased risk of higher microbial activity is predicted; or
 b) the frequency of biocide feed pulses is increased; or
 c) emptying the tower or the pulper where increased risk of higher microbial activity is predicted; or
 d) the frequency of emptying the tower is adjusted; or
 e) any combination of items a) to d).

A biocide or other controlling agent can be fed into the pulp in a tower or fibrous aqueous mass or into the pulp flow between process steps. The microbial control agent may be a biocide, reductive chemical or oxidative chemical.

The invention is illustrated below by the following non-limiting examples. It should be understood that the embodiments given in the description above and the examples are for illustrative purposes only, and that various changes and modifications are possible within the scope of the invention.

EXAMPLES

Example 1. Online Calculation of Risk Level for Higher Microbial Activity in a Broke Tower of a Board Machine Analysis of history data has shown that the broke tower studied in this example should be emptied once per day in order to prevent an increase in microbial activity in the tower. Risk limit for the level of the tower studied was 20% and predefined time was 1 day.

Signal from the tower level sensor was connected to a programmable logic circuit (PLC) or an industrial PC. Risk level was calculated continuously in the system (PLC or industrial PC).

Figure 1:
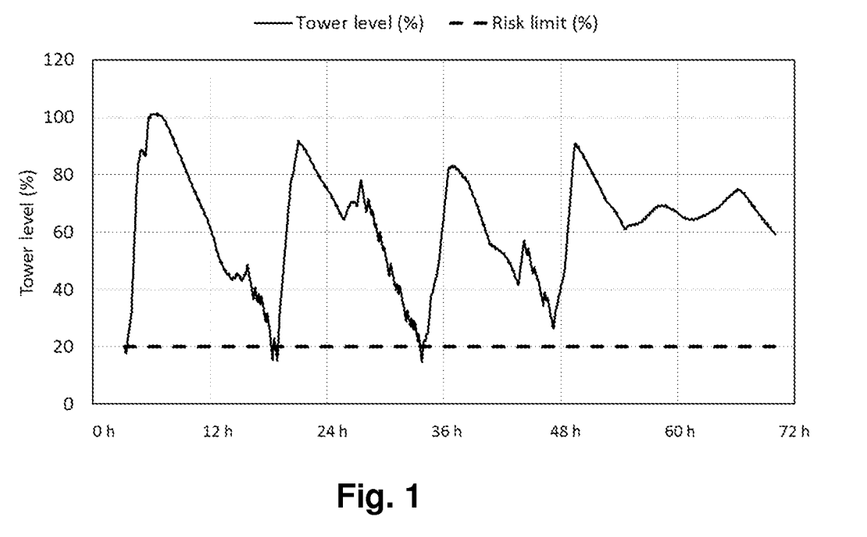
FIG. 1 shows an example of measured tower level and predefined limit for the surface level indicating risk of higher microbial activity ("risk limit for surface level")

Calculation was based on a timer which records the time as seconds, minutes, hours or days. The timer gets online information of the tower level every second. Timer resets the time to 0 s when the tower level was lowered to or below the predefined risk limit (20% or less than 20%). After resetting the time to zero, the timer starts to record the time again when the level has exceeded the risk limit (FIG. 1).

Figure 2:
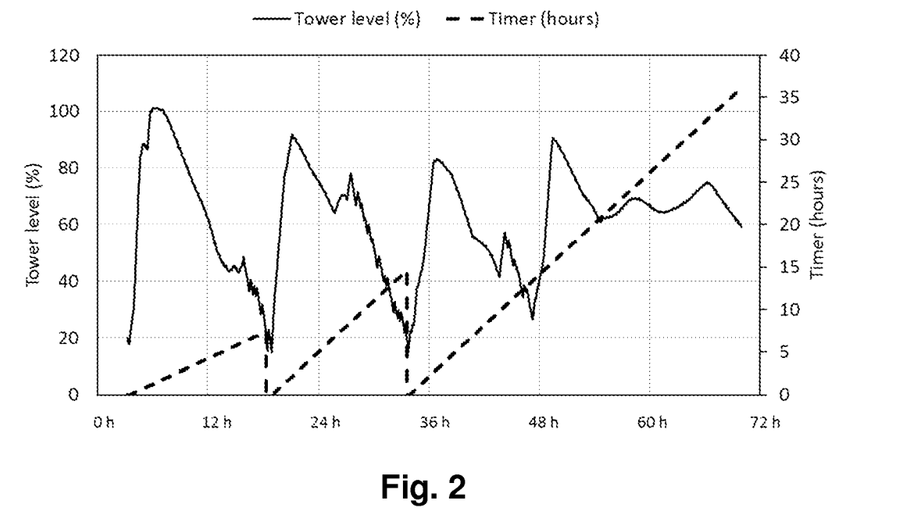
FIG. 2 shows an example of measured tower level and recorded time from the timer as hours.
Figure 3:
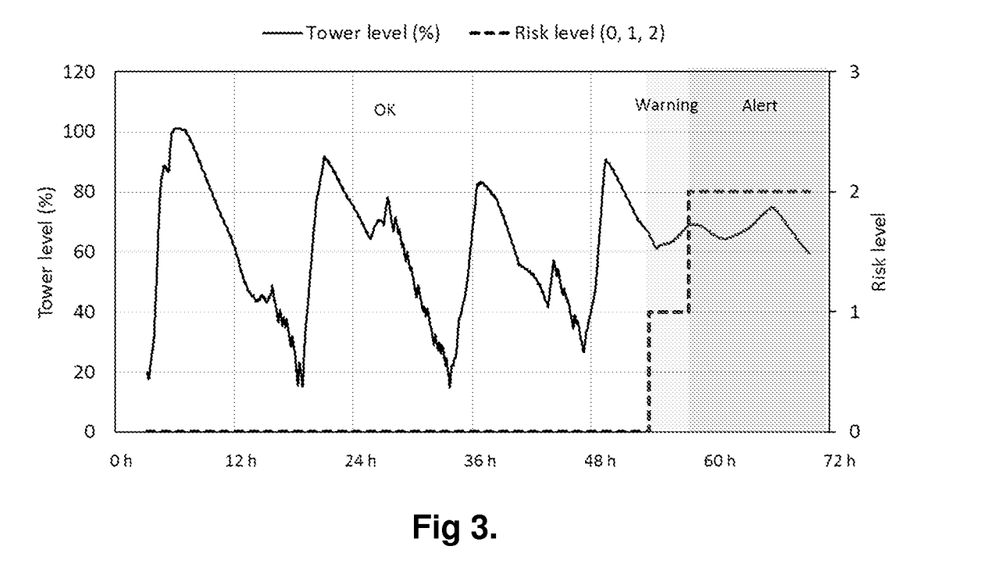
FIG. 3 shows an example of measured tower level and calculated risk level for increased risk for microbial activity.

When the recorded time was close to the predefined time, the system (e.g. PC, PLC) gives a warning. When the recorded time has met the predefined time, the system gives an alert (FIG. 2).
 If the recorded time is less than 20 hours, risk level is 0→no increased risk for microbial activity, no actions are needed.
 If the recorded time is more than 20 hours but less than 24 hours, risk level is 1→Warning, preparing for actions (e.g. mill visit, starting to prepare changes in biocide program)
 If the recorded time is more than 24 hours, risk level is 2→Alert, increased risk for microbial activity, actions are needed FIG. 3 shows a measured tower level and risk limit (safety limit).

Example 2. Online Calculation of Risk Level for Higher Microbial Activity in a Broke Tower Background: Analysis of history data has been shown that a broke tower should be emptied at least to or below a predefined surface level every 2.2 days in order to prevent increase in microbial activity in the tower and further quality issues in dry board.

Predefined risk limit for surface level: 25%
Predefined time: 2.2 days

Signal from the tower level sensor was connected to programmable logic (PLC) or industrial PC. Risk level was calculated continuously in the system (PLC or industrial PC).

Calculation of risk level was based on a timer which records a time e.g. as a seconds, minutes, hours or days. Timer gets online information from tower level. Timer resets the time to 0 s when the tower level was lowered to or below the predefined risk limit (=e.g. in this example case level is 25% or level is less than 25%). After resetting the time to zero, timer starts to record the time again when the level has exceeded the risk limit as shown in FIGS. 4 a and 4b.

When the recorded time is close to predefined time, the system (e.g. PC, PLC) gives warning. When the recorded time has met predefined time, the system gives alert, see FIG. 5.

If the recorded time is less than 1.8 days, risk level is 0→no increased risk for microbial activity, no actions are needed.

Figure 4A:
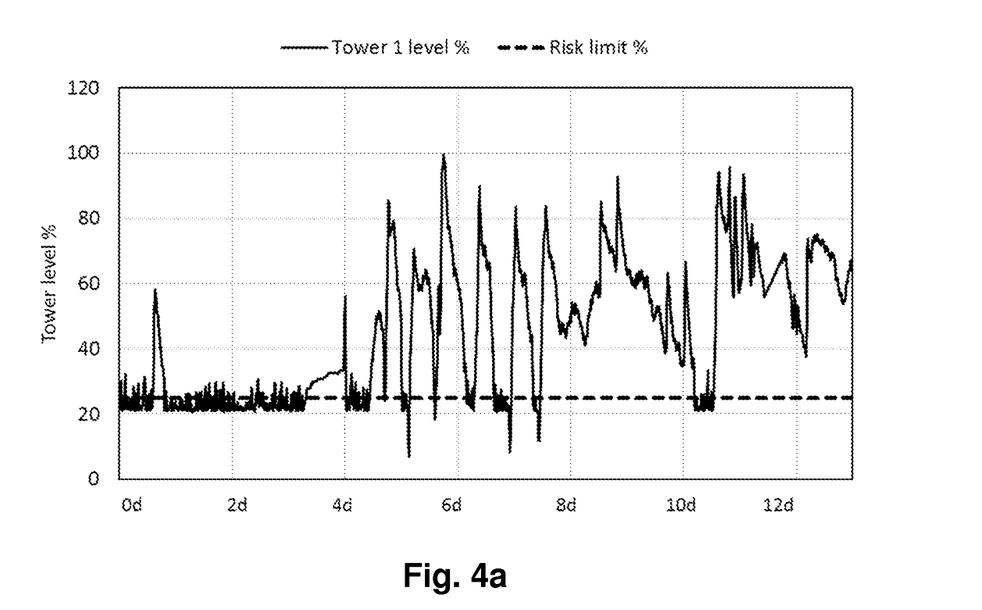
FIGS. 4a and 4b (a): Measured tower surface level and predefined risk limit. (b): Measured tower surface level, recorded time from the timer as days and predefined alert time (black horizontal line).
Figure 4B:
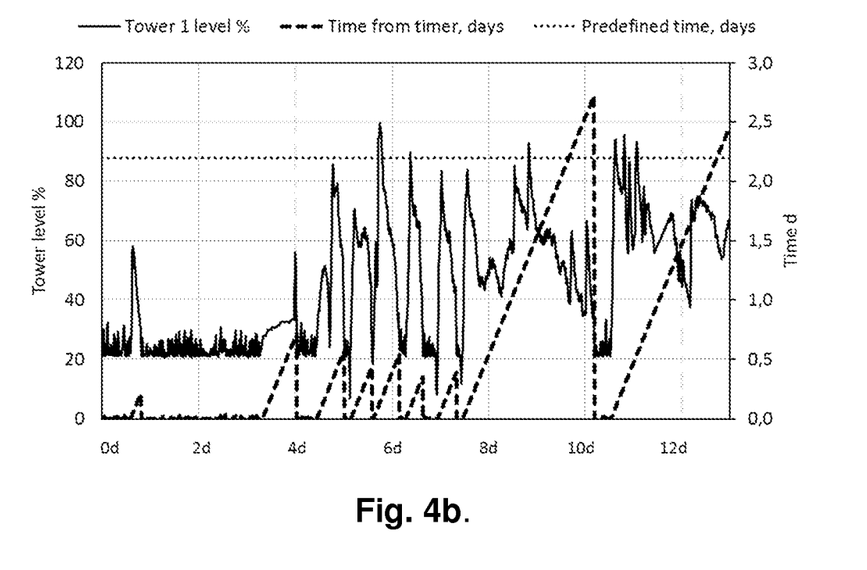

If the recorded time is more than 1.8 days but less than 2.2 days, risk level is 1→Warning If the recorded time is more than 2.2 days, risk level is 2→Alert, increased risk for microbial activity, actions are needed FIG. 4a shows measured tower surface level and predefined risk limit for surface level (i.e. predefined limit). FIG. 4b shows measured tower surface level, recorded time from the timer as days and predefined alert time (black horizontal line).

Figure 5:
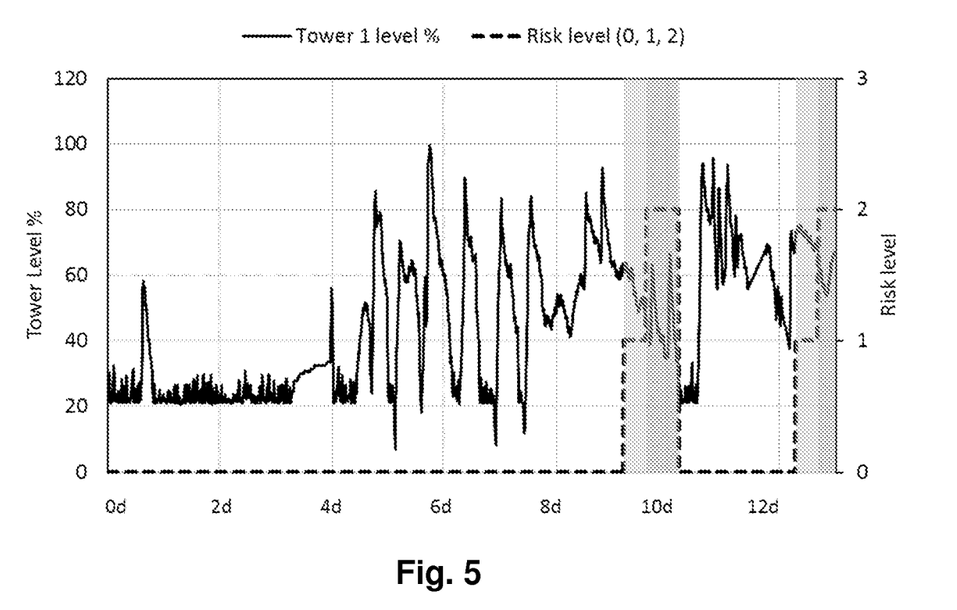
FIG. 5 shows measured tower surface level and calculated risk level for increased risk of microbial activity (0=ok, 1=warning, 2=alert).

FIG. 5 shows measured tower surface level and calculated risk level for increased risk of microbial activity (0=ok, 1=warning, 2=alert).

Figure 6A:
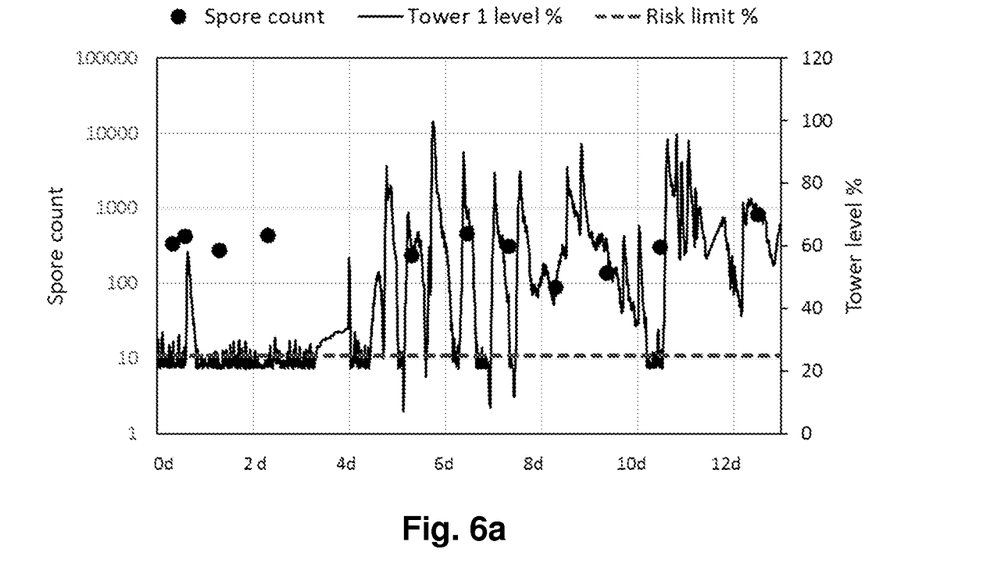
FIGS. 6a and 6b show a data of measured tower surface level and spore count in final board (a) and time from timer (b) during a 13 days' run period.
Figure 6B:
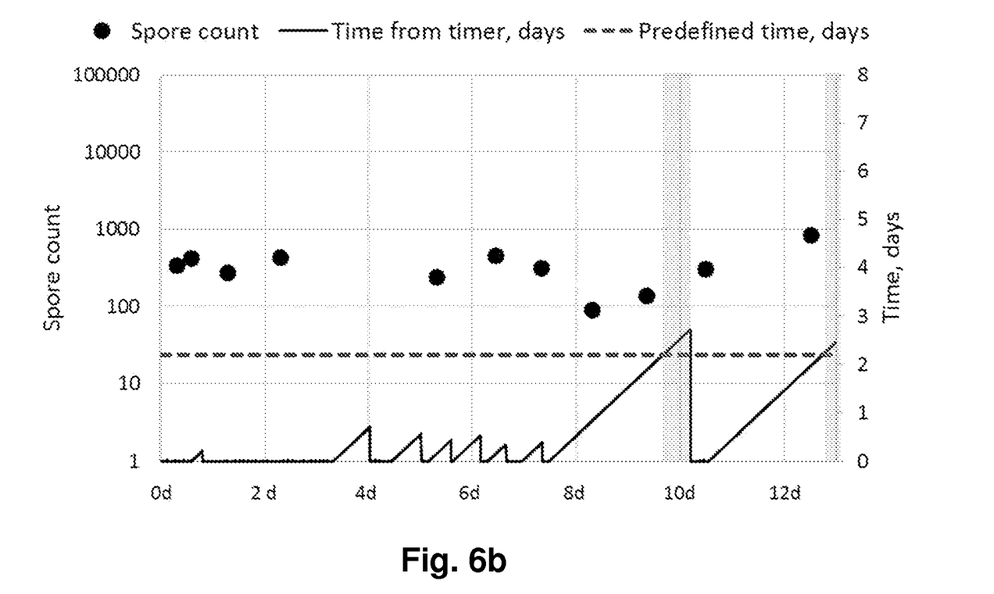
Figure 7A:
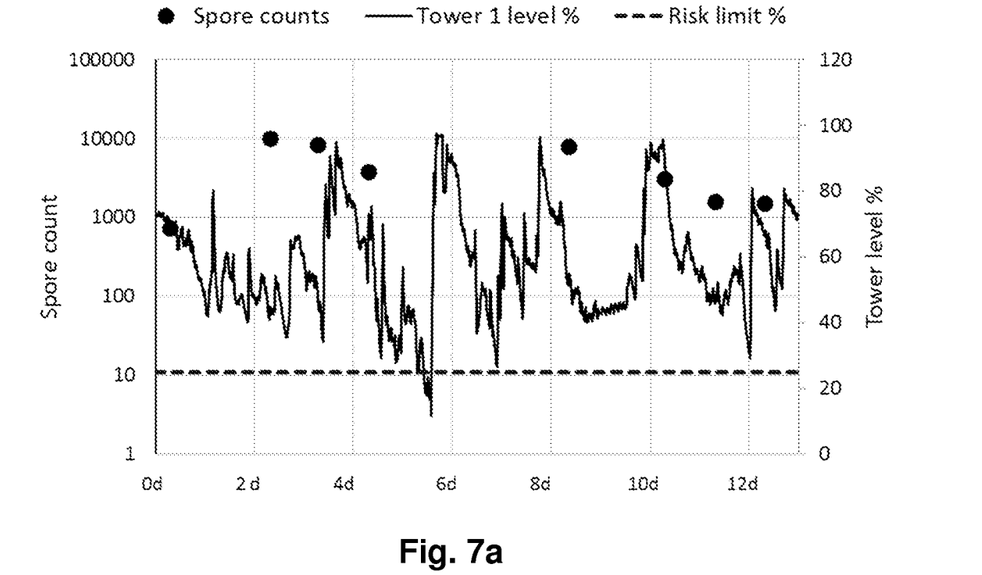
FIGS. 7a and 7b show data of measured tower surface level and spore count in final board (a) and time from timer (b) during a 13 days' run period during a second exemplary run period.
Figure 7B:
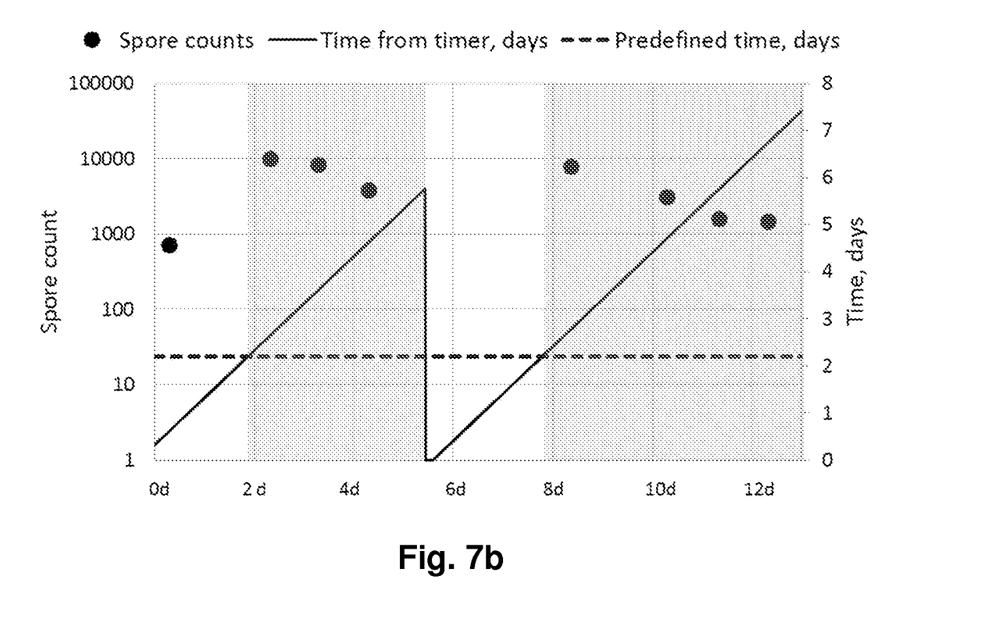
Figure 8A:
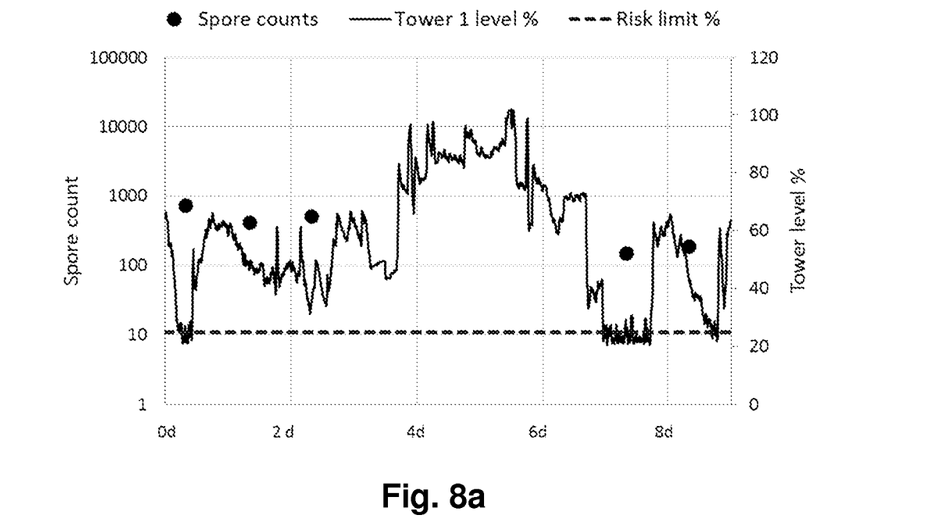
FIGS. 8a and 8b show data of measured tower surface level, spore count in final board (a), and time from timer (b) during a third exemplary run period.
Figure 8B:
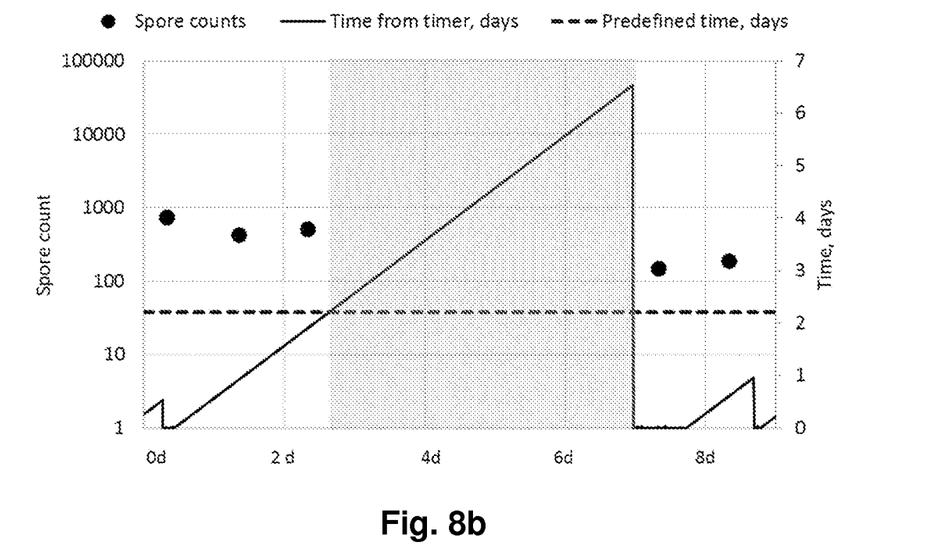

Example 3: Example of a Board Machine: Analysis of History Data, Quality of Dry Final Product Versus Risk Limit and Predefined Time of Broke Tower History data contained online tower level information and bacterial spore counts from dry board (laboratory analysis result). High quality board should contain a low amount of bacterial spores. In this mill the maximum limit for spore count is set to 1000 CFU/g. On the basis of the analysis following parameters were found:

Risk limit for the broke tower level: 25
Predefined time: 2.2 days
Examples are presented in FIGS. 6 to 8.

When recorded time is less than 2.2 days→Low risk for high spore count in end product (typical results <1000 CFU/g)

When recorded time is more than 2.2 days→Evaluated risk for high spore counts in end product (higher than 1000 CFU/g)

FIG. 6a shows data of measured tower surface level and spore count (CFU/g) in final board and FIG. 6b shows time from timer during a 13 days run period. There is only two occasions with increased risk (darkened area in chart on right), most of the period predefined time is below 2.2 and spore content in board is below 1000 CFU/g. Data clearly shows that the maximum surface level of storage tower itself is not the key parameter, because the tower regularly visits a surface level of over 80%, more important is that there are multiple moments where surface level visit such a low value that slowly moving (stagnant) areas of pulp are moving out from the tower. This enables maintaining of lower microbial activity in the tower, compared to a situation wherein pulp volume remains in storage for extended periods of time and microbial activity increases and spoils the quality of pulp.

FIG. 7a shows data of measured tower surface level and spore count (CFU/g) in final board and FIG. 7b shows time from timer during a 13 days run period. Most of the time is with increased risk (darkened area in chart on right) as the predefined time is over 2.2 days. During this period all measured samples of final board did exceed spore count 1000 CFU/g and thus did not meet quality target. Data clearly shows that the maximum surface level of storage tower itself is not the key parameter, because in this run period the tower surface level is frequently below 60%. More important is that there is only one moment where surface level visit such a low value that slowly moving (stagnant) areas of pulp can move out from the tower. This causes a situation most of the time there is slowly moving volumes of pulp that stay in storage tower for extended periods of time, demonstrate increasing microbial activity and this will cause loss of quality.

FIG. 8a. shows data of measured tower surface level, spore count in final board (7a)), and time from timer (FIG. 8b) during a third exemplary run period. When the predefined time is below 2.2 then the spore content in final dry board is below 1000 CFU/g.

The invention claimed is:

1. A method for controlling microbial status of a paper or board making process or quality of the dry board or paper obtained from said process, the method comprising:
   a) measuring at multiple time points a surface level and duration of time in at least one pulp storage tower, broke storage tower, or broke pulper, and determining at the same time points at least one key performance index (KPI) of said process or of paper or board obtained from said process;
   b) defining, using a computing device a correlation between said measured surface levels and durations of time in the at least one pulp storage tower, broke storage tower, or broke pulper in relation to determined values of the at least one KPI of said process or of paper or board obtained from said process;
   c) from the correlation defining a surface level limit and defining a limit of duration of time during which the measured surface level exceeds the surface level limit wherein the at least one KPI value was within an acceptable range;
   d) continuously monitoring surface level information of at least one pulp storage tower, broke tower or broke pulper, using a computer controlled tower level sensor and providing the surface level information in real time to computer controlled timer programmed to turn on when the surface level information exceeds the surface level limit and reset itself when the surface level information drops below a lower predetermined level;
   f) wherein an increased risk of higher microbial activity is determined when time recorded by the timer is as long or longer than the limit of duration of time defined in step c), and then the surface level of at least one pulp storage tower, broke tower or broke pulper is decreased and/or a microbial control agent is added into the process in response to the increased risk of higher microbial activity.

2. The method of claim 1, wherein in step f) decreasing surface level comprises emptying the pulp storage tower, the broke storage tower or the broke pulper where increased risk of higher microbial activity is determined, or adjusting frequency of emptying the pulp storage tower, the broke storage tower or broke pulper, or both; and adding of microbial control agent comprises increasing biocide feed quantity into the pulp storage tower, the broke storage tower or broke pulper and/or any process step before or after said tower or pulper where increased risk of higher microbial activity is determined, or increasing frequency of biocide feed pulses, or both.

3. The method according to claim 1, wherein in step d) monitoring surface level information is conducted in at least two pulp storage towers, broke storage towers or broke pulpers, and wherein an increased risk of higher microbial activity is determined when time recorded by the timers in each of the at least two pulp storage towers, broke storage towers or broke pulpers is as long or longer than the limit of duration of time defined in step c.

4. The method according to claim 1, wherein the at least one KPI value of said process is selected from pH, ORP (redox), rH, oxygen, dissolved oxygen, oxygen consumption, microbial amounts, microbial activity, amount of biofilm, and amount of malodorous compounds in the process.

5. The method according to claim 1, wherein the at least one KPI value of paper or board obtained from said process is selected from microbe content of said dry paper or board, or the number of quality defects of said dry paper or board.

\* \* \* \* \*